(12) United States Patent
Zastrozna

(10) Patent No.: US 11,266,453 B2
(45) Date of Patent: Mar. 8, 2022

(54) BONE COMPRESSION SCREWS AND RELATED SYSTEMS AND METHODS

(71) Applicant: DePuy Synthes Products, Inc., Raynham, MA (US)

(72) Inventor: Anna Zastrozna, Teaneck, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/137,584

(22) Filed: Sep. 21, 2018

(65) Prior Publication Data

US 2020/0093525 A1 Mar. 26, 2020

(51) Int. Cl.
*A61B 17/86* (2006.01)
*A61B 17/68* (2006.01)

(52) U.S. Cl.
CPC .......... *A61B 17/863* (2013.01); *A61B 17/864* (2013.01); *A61B 17/866* (2013.01); *A61B 2017/681* (2013.01); *A61B 2017/8655* (2013.01)

(58) Field of Classification Search
CPC ................ A61B 17/863; A61B 17/864; A61B 2017/681; A61B 2017/8655; A61B 17/86–17/866
See application file for complete search history.

(56) References Cited

U.S. PATENT DOCUMENTS

| | | | | |
|---|---|---|---|---|
| 2,382,019 A | * | 8/1945 | Miller | F16B 25/0057 411/378 |
| 5,147,363 A | * | 9/1992 | Harle | A61B 17/8605 606/305 |

(Continued)

FOREIGN PATENT DOCUMENTS

| | | |
|---|---|---|
| EP | 2422712 A2 | 2/2012 |
| EP | 2422713 A2 | 2/2012 |

(Continued)

OTHER PUBLICATIONS

Arthrex, Compression FT Screw System Brochure, 2014, 6 pages.
Acumed, Acutrak 2, Headless Compression Screw System, Surgical Technique, 2014, 28 pages.

*Primary Examiner* — Zade Coley
(74) *Attorney, Agent, or Firm* — BakerHostetler

(57) ABSTRACT

A method of shaping a bone screw with an automated device having a CNC unit includes rotating a blank coupled to a spindle about an axis defined by a coordinate system of the CNC unit, advancing a cutting tool proximally through an exterior of the blank at a speed to form a helical thread along a shaft, and reducing the speed to provide a variable, proximally decreasing pitch along at least a portion of the shaft. A first cutting tool is automatically transitioned toward disengagement from the blank when 1) a relative axial position between the first cutting tool and the blank coincides with a first coordinate of a predetermined location, and 2) a relative rotational position between the first cutting tool and the blank coincides with a second coordinate of the predetermined location. The first coordinate is along the axis, the second coordinate is an angular position about the axis, and the first and second coordinates are defined by the coordinate system. A second cutting tool is moved into engagement with the exterior of the blank so that the second cutting tool engages the blank substantially at the predetermined location, in a manner enabling continuation of the thread.

12 Claims, 7 Drawing Sheets

(56) References Cited

U.S. PATENT DOCUMENTS

| | | | |
|---|---|---|---|
| 5,403,136 A * | 4/1995 | Mathys | A61B 17/744 411/263 |
| 5,562,672 A | 10/1996 | Huebner et al. | |
| 5,871,486 A | 2/1999 | Huebner et al. | |
| 5,964,768 A | 10/1999 | Huebner | |
| 6,030,162 A * | 2/2000 | Huebner | A61B 17/1682 411/263 |
| 6,299,615 B1 | 10/2001 | Huebner | |
| 6,984,235 B2 | 1/2006 | Huebner et al. | |
| 7,235,078 B2 * | 6/2007 | West, Jr. | A61B 17/8875 411/310 |
| 8,070,786 B2 | 12/2011 | Huebner et al. | |
| 8,075,604 B2 * | 12/2011 | Denis | A61B 17/7032 606/315 |
| 8,192,199 B2 * | 6/2012 | Arni | A61C 8/0074 433/174 |
| 8,491,302 B2 * | 7/2013 | Arni | A61C 8/0022 433/173 |
| 8,998,612 B2 * | 4/2015 | Park | A61C 8/0022 433/172 |
| 9,055,986 B1 * | 6/2015 | Whipple | A61B 17/8625 |
| 9,161,793 B2 * | 10/2015 | Huebner | A61B 17/844 |
| 9,622,739 B2 * | 4/2017 | Dreyfuss | A61B 17/0401 |
| 9,956,018 B2 * | 5/2018 | Peukert | A61B 17/7032 |
| 9,993,275 B2 * | 6/2018 | Mildner | A61B 17/863 |
| 10,058,368 B2 * | 8/2018 | Orbay | A61B 17/8625 |
| 2010/0145397 A1 * | 6/2010 | Overes | A61B 17/725 606/319 |
| 2011/0144703 A1 * | 6/2011 | Krause | A61B 17/8625 606/309 |
| 2012/0130433 A1 * | 5/2012 | Huebner | A61B 17/863 606/300 |
| 2013/0211468 A1 * | 8/2013 | Huebner | A61B 17/863 606/328 |
| 2014/0012334 A1 * | 1/2014 | Armstrong | A61B 17/863 606/309 |
| 2016/0038203 A1 * | 2/2016 | Huebner | A61B 17/864 606/304 |
| 2017/0095279 A1 * | 4/2017 | Bare | A61B 17/8057 |
| 2017/0196608 A1 * | 7/2017 | Castaneda | A61B 17/863 |
| 2017/0196612 A1 * | 7/2017 | Castaneda | A61B 17/8635 |
| 2018/0092677 A1 * | 4/2018 | Peterson | A61B 17/844 |
| 2018/0303529 A1 | 10/2018 | Zastronzna | |
| 2019/0262047 A1 * | 8/2019 | Sommers | A61B 17/863 |

FOREIGN PATENT DOCUMENTS

| | | |
|---|---|---|
| GB | 2355505 A | 4/2001 |
| WO | 95/15727 A1 | 6/1995 |

* cited by examiner

BONE COMPRESSION SCREWS AND RELATED SYSTEMS AND METHODS

TECHNICAL FIELD

The present invention relates to bone screws, particularly to bone screws having external threads with transitions in the thread pitch.

BACKGROUND

Various types of bone screws are designed to cause compression of bone material alongside the screw as the screw is driven into bone. Such bone screws can be categorized as "compression bone screws" or simply "compression screws." Compression screws are particularly useful for, among other things, anatomical reduction between two portions of bone, such as for treatment of a fracture, fusion, or osteotomy.

One category of compression screw involves screws that employ a distal thread pitch that is greater than a proximal thread pitch. This category can include partially threaded, multi-pitch screws. It can also include screws that are fully threaded along their length. To achieve compression, some fully threaded compression screws have a single-lead thread that defines a proximally decreasing thread pitch, at least along a portion of the screw. Such bone screws can be referred to as "variable pitch screws." Such variable pitch screws have been shown to achieve favorable results in use, particularly in regard to bone compression characteristics.

However, variable pitch screws also present significant challenges, in design as well as operation. One such operational challenge is that variable pitch screws can require a higher amount of insertion torque relative to other types of compression screws, such as partially threaded screws. Thus, prior art variable pitch screws typically require pre-drilling prior to insertion. The insertion torque can also impose limits to the screw's design, such as the screw length, for example.

Other design challenges involve the limitations inherent in the state-of-the-art manufacturing machines and systems for manufacturing bone screws. On such category of machines are multi-axis, multi-tool, high speed, Computer Numerical Control (CNC) lathes, commonly referred to in the art as "Swiss Lathes." Although such lathes can incorporate high-speed, high precision thread forming tools, such as "thread whirling tools" or simply "whirling tools," these thread-forming tools have limitations, particularly at speeds and economies necessary for industrial scale bone screw manufacturing. For example, as the thread pitch decreases (thus also decreasing the helix angle), the whirling tool can begin to cross-thread the screw. Cross-threading may also occur when the distance between the whirling tool and the central axis of the screw increases (also decreasing the helix angle) while thread forming. One way in which manufacturers avoid cross-threading is by limiting the amount of increase in the distance of the whirling tool from the central axis of the screw. This limits the increase in the minor thread diameter (also referred to as the "core" diameter) and the amount of space available for the drive socket. However, such screws lack the associated benefits of having a defined head.

SUMMARY

According to an embodiment of the present disclosure, a bone screw includes a body extending from a proximal end to a distal end spaced from the proximal end in a distal direction. The body defines a central axis oriented along the distal direction. The body defines a core surface spaced from the central axis along a radial direction that is substantially perpendicular to the longitudinal direction. The body includes a head having a main head portion and a neck spaced from the main head portion in the distal direction. The main head portion defines a main head length along the distal direction. The core surface within the main head portion defines a minor head diameter value along the radial direction for substantially an entirety of the main head length. The body includes a shaft that extends from the neck to the distal end in the distal direction. The core surface at the shaft defines 1) a shaft length along the distal direction, and 2) a minor shaft diameter value along the radial direction for at least a majority of the shaft length. The main head length is at least about 2.0 mm. A ratio of the minor head diameter value to the minor shaft diameter value is at least about 1.2:1. The body includes a thread that extends outward from the core surface along the radial direction. The thread extending along a single, continuous, helical thread path that traverses at least a portion of the shaft, the neck, and at least some of the main head portion. The thread defines 1), a pitch region that extends along the shaft and defines a pitch of the thread, and 2) a second pitch region that extends from a shared boundary with the pitch region, encompasses the head, and defines a second pitch of the thread, such that the second pitch is less than the pitch, and the pitch transitions to the second pitch at the shared boundary.

According to another embodiment of the present disclosure, a method of shaping a bone screw with an automated thread-forming device having a CNC unit that defines a coordinate system in three-dimensional space includes rotating a blank rigidly coupled to a spindle about an axis defined by the coordinate system, advancing a first cutting tool through an exterior of the blank in a proximal direction oriented along the axis and at a speed during the rotating step so as to form a helical thread along a shaft of the bone screw, and reducing the speed during the advancing step, thereby providing a variable, proximally decreasing pitch along at least a portion of the shaft. The method includes transitioning the first cutting tool toward disengagement from the blank under automated control of the CNC unit when 1) a relative axial position between the first cutting tool and the blank coincides with a first coordinate of a predetermined location between the first cutting tool and the blank, and 2) a relative rotational position between the first cutting tool and the blank coincides with a second coordinate of the predetermined location, wherein the first coordinate is along the axis, the second coordinate is an angular position about the axis, and the first and second coordinates are defined by the coordinate system. The method includes moving a second cutting tool into engagement with the exterior of the blank under automated control of the CNC unit so that the second cutting tool engages the blank substantially at the predetermined location in a manner enabling continuation of the helical thread.

BRIEF DESCRIPTION OF THE DRAWINGS

The foregoing summary, as well as the following detailed description of illustrative embodiments of the bone screw of the present application, will be better understood when read in conjunction with the appended drawings. For the purposes of illustrating the bone screw of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

As used herein with reference to a bone screw, the term "fully threaded" refers to an external thread that extends substantially along an entire length of the bone screw.

As used herein with reference to threading, the term "multi-pitch" encompasses variable pitch threads as described above.

The embodiments described below pertain to bone compression screws that employ a continuous, multi-pitch external thread extending along at least a portion of the shaft and along at least a portion of a defined head. Currently, manufacturers avoid incorporating a head into continuous thread, variable pitch compression screws. One reason for this is because high-speed thread-forming tools, such as whirling tools, have a tendency to begin cross-threading as they increase their radial distance from the central screw axis at a neck portion of the head, particularly when the helix angle of the thread also changes with increasing diameter. The embodiments described below incorporate a predetermined thread transition zone into the thread geometry. As will be described in more detail below, the thread transition zone allows a first cutting tool (i.e., the tool used to form the thread along the shaft) to withdraw from the screw under control of a CNC unit while a second cutting tool, also under control of the CNC unit, engages the screw in the thread transition zone to continue the thread in a continuous manner. This technical advancement allows, among other things, fully threaded, variable pitch compression screws to have a defined head at the proximal end.

Figure 1:
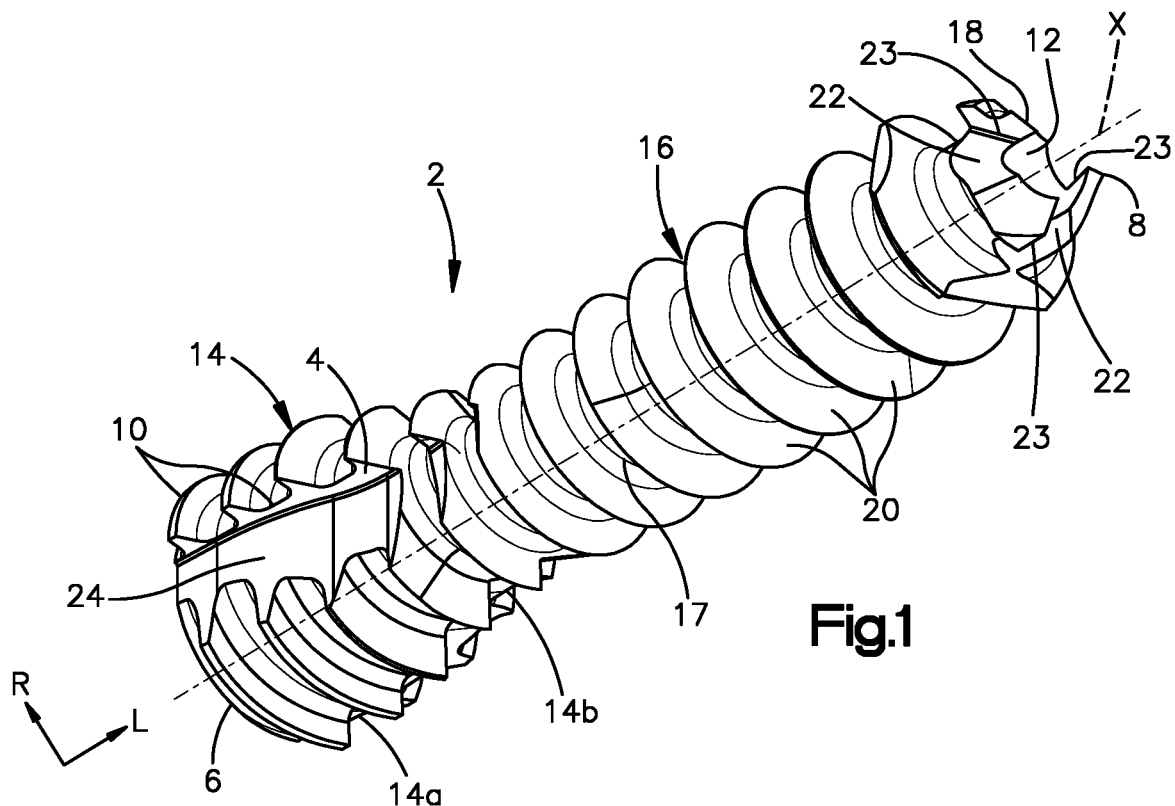
FIG. 1 is a perspective view of a bone screw having a continuous external thread with at least one thread transition zone, according to an embodiment of the present disclosure.

Referring to FIG. 1, a bone screw 2 is shown having features configured to compress bone material alongside the bone screw 2 as the screw 2 advances through the bone material. The bone screw 2 includes a body 4 defining a proximal end 6 and a distal end 8 spaced from each other along a longitudinal direction L. The body 4 can be formed of a bio-compatible material, such as titanium, a titanium alloy (such as a titanium-aluminum-niobium ("TAN") alloy), stainless steel, or any combination thereof, by way of non-limiting example. The body 4 can define a central axis X oriented along the longitudinal direction L. Accordingly, the central axis X can also be referred to as a "longitudinal" axis of the screw 2. Additionally, the longitudinal direction L can be referred to as an "axial" direction. The body 4 can define an outer surface 10 that is spaced from the central axis X along a radial direction R that is substantially perpendicular to the longitudinal direction L. The outer surface 10 can extend from the proximal end 6 toward the distal end 8.

As referred to herein, the radial direction R is bi-directional, and includes mono-directional radially outward and radially inward components, wherein "radially outward" means in the radial direction R away from central axis X, and "radially inward" means in the radial direction R toward the central axis X. The bone screw 2 can also define a distal direction that extends from the proximal end 6 to the distal end 8 along the central axis X. The bone screw 2 can also define a proximal direction that extends from the distal end 8 to the proximal end 6 along the central axis X and is opposite the distal direction. As referred to herein, the distal and proximal directions are each mono-directional components of the bi-directional longitudinal direction L.

The screw body 4 can define a cannulation 12 (shown in more detail in FIG. 6) extending through the body 4 from the proximal end 6 to the distal end 8. The cannulation 12 can be a through-bore that is configured to receive a guide wire therein in a manner allowing the bone screw 2 to move along the guide wire to a target location in tissue of a patient. An interior surface 13 of the body 4 within the cannulation 12 can be substantially smooth and cylindrical, although other geometries are within the scope of the present embodiments.

The body 4 defines a head 14 and a shaft 16 extending from the head 14 in the distal direction. The head 14 includes a main head portion 14a that can extend proximally to the proximal end 6 of the bone screw 2. The head 14 includes a neck 14b that extends distally from the main head portion 14a to the shaft 16. The neck 14b tapers distally toward the central axis X. The shaft 16 can include a main shaft portion 17 that extends distally from the neck 14b, and can also include a tip portion 18 that is spaced distally from the main shaft portion 17 and extends to the distal end 8 of the bone screw 2. At the tip portion 18, the outer surface 10 of the body 4 can taper distally toward the central axis X to facilitate penetration of bone material. The outer surface 10 of the body 4 defines an external thread 20 (also referred to herein as the "thread") that extends along the shaft 16 and the head 14, as described in more detail below.

The bone screw 2 can include one or more cutting features for cutting, penetrating and/or slicing bone material in a manner facilitating insertion of the bone screw 2 into bone. For example, the shaft 16 can include one or more cutting flutes 22 that extend to the distal end 8 of the bone screw 2. Such cutting flute(s) 22 can also referred to as "distal cutting flute(s)." It is to be appreciated that, in some embodiments, the distal cutting flute(s) 22 can extend proximally to the main shaft portion 17. Each distal cutting flute 22 can intersect the cannulation 12 distally. The one or more distal cutting flutes 22 can define one or more cutting teeth 23 circumferentially spaced between the cutting flutes 22. Each of the one or more cutting teeth 23 can define a distal cutting tip that is coincident with the distal end 8 of the bone screw 2. The distal cutting flutes 22 can circumferentially interrupt the thread 20. The one or more distal cutting flutes 22 and the one or more cutting teeth 23 can be configured as more fully described in U.S. patent application Ser. No. 15/958, 541, filed Apr. 20, 2018, in the name of Zastrozna (the "Zastrozna Reference"), the entire disclosure of which is hereby incorporated by reference into this patent application. The head 14 can also define one or more cutting flutes 24 for facilitating insertion of the bone screw 2 into bone 2. The cutting flute(s) 24 of the head 14 can also be referred to as "head cutting flute(s)." It is to be appreciated that, in some embodiments, the head cutting flute(s) 24 can extend distally to the shaft 16.

Figure 2:
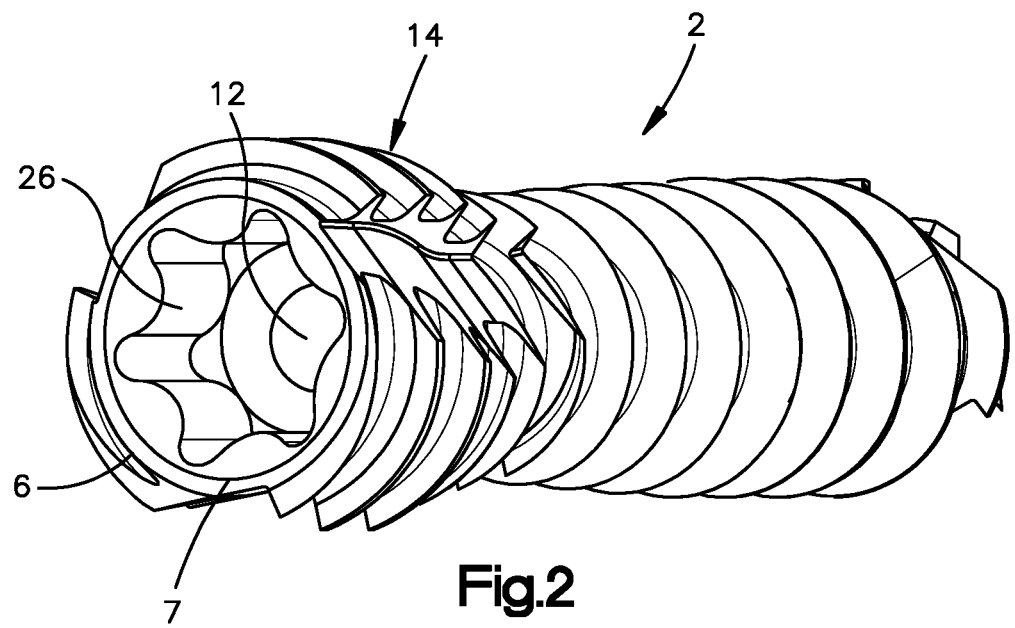
FIG. 2 is a perspective view of a socket at a proximal end of the bone screw shown in FIG. 1.

As shown in FIG. 2, the head 14 can define a socket 26 extending from the proximal end 6 of the screw 2 in the distal direction. The socket 26 can be configured to receive a driving tool operated by a physician. As shown, the socket 26 can have a star-hex configuration, although other socket configurations are within the scope of the disclosed embodiments. The socket 26 can be in communication with the cannulation 12. The socket 26 can extend distally from a proximal-most surface 7 of the bone screw 2. The proximal-most surface 7 can be substantially planar. The proximal-most surface 7 can be substantially orthogonal with respect to the central axis X. It is to be appreciated that one of the benefits of providing the bone screw 2 with a defined head 14 is that the socket 26 can be enlarged accordingly and can be sized to work with instrumentation (such as driving instruments) common with other types of bone screws. Another benefit of the defined head 14 is better coupling of the head 14 with a chuck and/or collet of a thread-forming tool.

Figure 3:
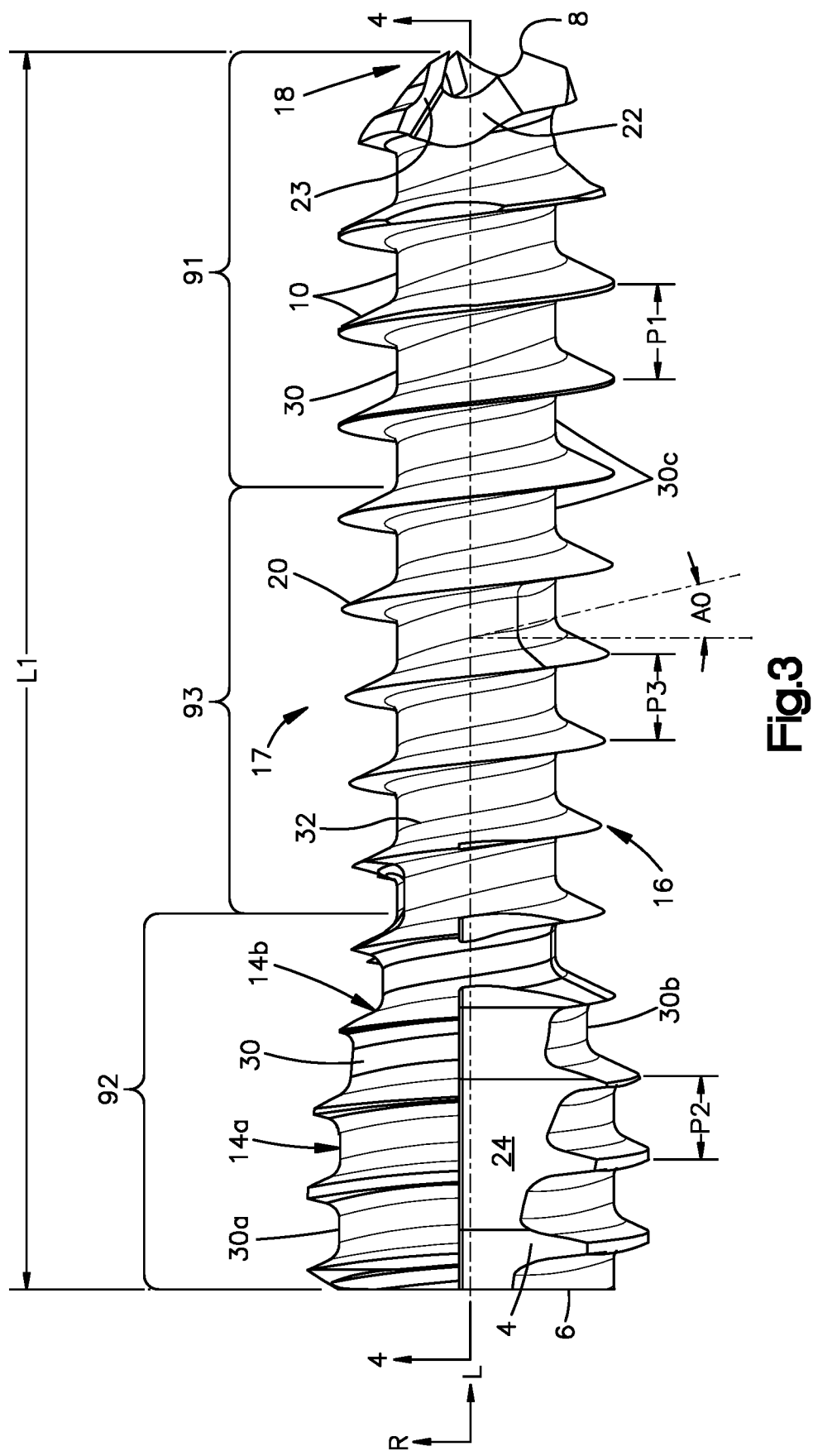
FIG. 3 is a side view of the bone screw shown in FIG. 1.

Referring now to FIG. 3, the outer surface 10 of the body 4 defines a primary screw surface 30 (also referred to herein as the "core surface" or "core"). The core 30 preferably extends from the proximal end 6 substantially to the distal end 8 of the bone screw 2. The thread 20 extends radially outward from the core 30. At any portion along the thread 20, a minor thread diameter is measured at the core 30, while a major thread diameter is measured at a crest of the thread 20. A portion of the core 30 along the main head portion 14a can be referred to as the main head core 30a. A portion of the core 30 along the neck 14b can be referred to as the neck core 30b. A portion of the core 30 along the main shaft portion 17 can be referred to as the main shaft core 30c.

The thread 20 extends along a single, continuous, helical thread path 32 that longitudinally traverses at least a portion of the shaft 16, the entire neck 14b, and at least a portion of the main head portion 14a. The thread path 32 defines a helix angle A0 with respect to the central axis X. In some embodiments, the thread path 32 can longitudinally traverse the entire shaft 16 and extend within the tip portion 18. In additional embodiments, the thread path 32 can longitudinally traverse the entire tip portion 18. In further embodiments, the thread path 32 can longitudinally traverse the entire head 14, including the entire main head portion 14a. In a preferred embodiment, the thread path 32 longitudinally traverses substantially an entire length L1 of the bone screw 2, from the distal end 8 to the proximal end 6. The thread 20 extends along the helical thread path 32. In the present embodiment, the thread 20 extends continuously along the helical thread path 32, except where the thread 20 is circumferentially interrupted by the distal cutting flute(s) 22 and the head cutting flute(s) 24. In other embodiments, the bone screw 2 can optionally include other features that interrupt the thread 20. Preferably, the helical thread path 32 itself it not interrupted by the any features of the bone screw 2. As a conceptual matter, it is to be appreciated that, in some methods of forming the bone screw 2, the thread 20 can be formed as a single, continuous, uninterrupted helical thread along the length of the screw body 4; subsequently, one or more features, such as head cutting flutes 24, can be machined into the threaded screw body, thus circumferentially interrupting the thread 20.

The helical thread path 32 can be characterized as having a plurality of helical thread path segments. Similarly, the thread 20 can be characterized as having a plurality of thread portions segments extending along the helical thread path 32.

The bone screw 2 can define a plurality of thread regions, in which at least one parameter value of the thread 20, such as thread pitch, differs from that within another of the plurality of thread regions. As shown, the bone screw 2 can define a first or distal thread region 91, a second or proximal thread region 92, and a third or intermediate thread region 93. The distal thread region 91 extends along a distal portion of the shaft 16 and defines a first or distal pitch P1. The proximal thread region 92 preferably encompasses the head 14 (including the main head portion 14a and the neck 14b) and defines a second or proximal pitch P2. The intermediate thread region 93 extends along the main shaft portion 17 and defines a third or intermediate pitch P3. The proximal pitch P2 is less than the distal pitch P1. This allows the thread 20 to compress bone material alongside the bone screw 2 between the distal and proximal thread regions 91, 92 as the bone screw 2 is advanced through bone.

In a preferred embodiment, the distal pitch P1 is constant throughout the distal thread region 91, the proximal pitch P2 is constant throughout the proximal thread region 92, and the intermediate pitch P3 is a variable pitch that decreases proximally from the distal pitch P1 to the proximal pitch P2. In such embodiments, the intermediate pitch P3 can be substantially equivalent to the distal pitch P1 at a boundary between the intermediate thread region 93 and the distal thread region 91, and can be substantially equivalent to the proximal pitch P2 at a boundary between the intermediate thread region 93 and the proximal thread region 91. The intermediate pitch P3 can decrease proximally at a substantially constant rate of change per unit of length along the longitudinal direction L (and thus also at a constant rate of change per revolution about the central axis X). In other embodiments, the intermediate pitch P3 can decrease proximally at a non-constant rate of change. In yet other embodiments, the intermediate pitch P3 can be constant along at least a portion of the intermediate thread region 93, and can be no greater than the distal pitch P1 and no less than the proximal pitch P2.

The distal pitch P1 can be in a range of about 0.50 mm to about 3.00 mm. In other embodiments, the distal pitch P1 can be in a range of about 0.55 mm to about 2.75 mm. In additional embodiments, the distal pitch P1 can be in a range of about 1.00 mm to about 2.25 mm.

The proximal pitch P2 can be in a range of about 0.40 mm to about 2.80 mm. In other embodiments, the proximal pitch P2 can be in a range of about 0.50 mm to about 2.50 mm. In additional embodiments, the proximal pitch P2 can be in a range of about 0.85 mm to about 2.00 mm.

A ratio of the distal pitch P1 to the proximal pitch P2 can be in the range of about 1.01:1 to about 2.00:1. In other embodiments, the ratio of the distal pitch P1 to the proximal pitch P2 can be in the range of about 1.03:1 to about 1.50:1. In additional embodiments, the ratio of the distal pitch P1 to the proximal pitch P2 can be in the range of about 1.05:1 to about 1.25:1. In further embodiments, the ratio of the distal pitch P1 to the proximal pitch P2 can be in the range of about 1.06:1 to about 1.13:1.

It is to be appreciated that, in some embodiments, the bone screw 2 can define a total of two thread regions. In such embodiments, the distal thread region 91 can extend to, and share a boundary with, the proximal thread region 92. In such embodiments, the distal thread region 91 can have a substantially constant pitch or a variable pitch along its entire length. In additional embodiments, the bone screw 2 can define a single thread region (i.e., the "first" thread region 91). In such embodiments, the thread 20 can have a constant pitch along its entire length.

Figure 4:
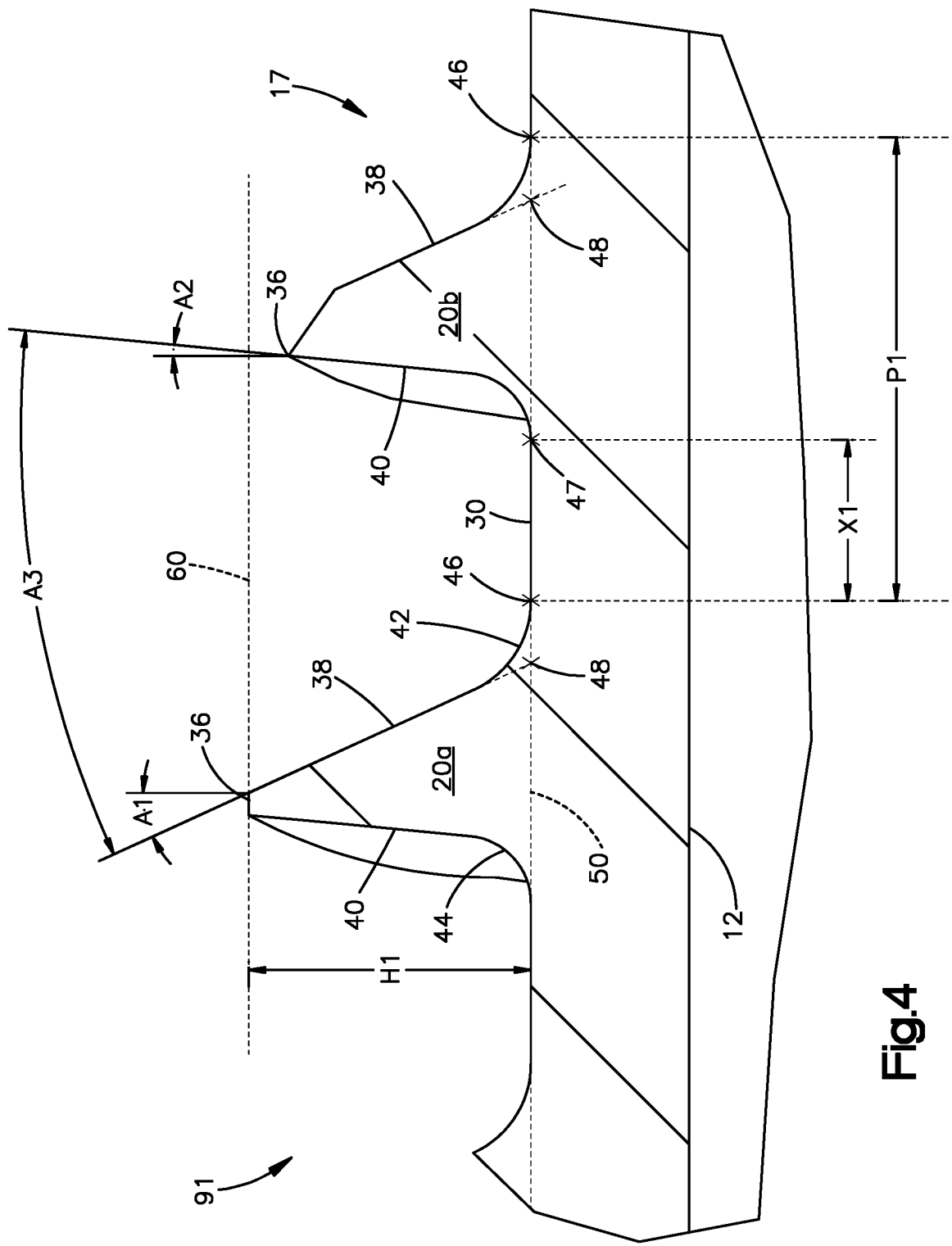
FIG. 4 is an enlarged, sectional view of a distal portion of the thread taken along section line 4-4 as shown in FIG. 3, which section line 4-4 contains a central axis of the bone screw.

Referring now to FIG. 4, additional parameters of the thread 20 will be described with reference to a pair of adjacent thread segments 20a, 20b located within the distal thread region 91. Particularly, distal shaft thread segments 20a, 20b are located in a portion of the distal thread region 91 that coincides with the main shaft portion 17. It is to be appreciated that the thread parameters discussed below with reference to thread segments 20a, 20b can also apply to the thread 20 in distal and intermediate thread regions 92, 93. Differences between the parameter values in the various thread regions 91, 92, 93 will be described in more detail below.

The thread 20 extends radially outward from a thread root (i.e., the core 30) to a thread crest 36. The thread 20 includes a distal flank 38 on a distal side of the thread 20 and a proximal flank 40 on a proximal side of the thread. Each of the distal and proximal flanks 38, 40 extends between the core 30 and the crest 36. The thread 20 preferably includes distal and proximal relief surfaces 42, 44 extending between the distal and proximal flanks 38, 40, respectively, and the core 30. The relief surfaces 42, 44 are preferably radiused to reduce stress concentration at the radially inner portions of the thread 20. The crest 36 can also have a geometry configured to reduce stress concentrations at the radially outermost portions of the thread 20.

The crest 36 can have a flat or "truncated" profile at one or more of the thread segments (such as at thread segment 20a) in a reference plane that contains the central axis X. The crest 36 geometry of one or more thread segments can be affected by other parameters. For example, as shown at thread segment 20b, a portion of the crest 36 can be cropped, such as by a portion of a cutting flute 22, for example. It is to be appreciated that, as used herein, the terms "truncate," "truncated," and their derivatives are not used synonymously with the terms "crop," "cropped," and their derivatives. The "truncate," "truncated," and their derivatives, as used herein with reference to the thread 20, refers to an act affecting the crest 36 profile as a primary function. The term "crop," as used herein with reference to the thread 20, refers to an act affecting the crest 36 profile as a secondary (or tertiary, etc.) function, such as forming cutting flutes or reducing the pitch, by way of non-limiting examples.

In the reference plane, each thread segment can have a thread profile (also referred to in the art as a "threadform") defined by the distal core 30, the distal relief surface 42, the distal flank 38, the crest 36, the proximal flank 40, the proximal relief surface 44, and the proximal core 30. In a thread segment, one or both of the distal and proximal flanks 38, 40 can have a linear profile in the reference plane. For example, the distal flank 38 can have a linear profile and can be offset from a radial axis at a first or distal flank angle A1. The proximal flank 40 can have a linear profile and can be offset from the radial direction at a second or proximal flank angle A2. Preferably, the proximal flank angle A2 is steeper than the distal flank angle A1, which, among other things, can help prevent the bone screw 20 from backing out of a portion of bone after insertion. The thread 20 defines a thread angle A3 measured between the distal flank 38 and the proximal flank 40 of longitudinally adjacent thread segments, such as distal shaft thread segments 20a, 20b. The thread 20 defines a primary thread height H1, measured from the core 30 to an uncropped crest 36.

In some embodiments, one or more of the distal and proximal flanks 38, 40 can have a curved profile in the reference plane. In such embodiments, the respective slope angle A1, A2 and thread angle A3 can be measured from a tangent line that intersects the curved-profile flank at a radial midpoint between the crest 36 and core 30.

The distal flank angle A1 can be in a range of about 1° to about 45°. In other embodiments, the distal flank angle A1 can be in a range of about 20° to about 40°. In additional embodiments, the distal flank angle A1 can be in a range of about 25° to about 35°.

The proximal flank angle A2 can be in a range of about 0° to about 30°. In other embodiments, the proximal flank angle A2 can be in a range of about 2° to about 12°. In additional embodiments, the proximal flank angle A2 can be about 5°.

The thread angle A3 can be in a range of about 10° to about 90°. In other embodiments, the thread angle A3 can be in a range of about 20° to about 50°. In additional embodiments, the thread angle A3 can be in a range of about 30° to about 40°.

The primary thread height H1 of distal shaft thread segments 20a, 20b can be in a range of about 0.10 mm to about 2.00 mm. In other embodiments, primary thread height H1 can be in a range of about 0.17 mm to about 1.75 mm. In additional embodiments, primary thread height H1 can be in a range of about 0.20 mm to about 0.85 mm. It is to be appreciated that cropping can reduce the height of distal shaft thread segments 20a, 20b, at least along a circumferential portion thereof.

With continued reference to FIG. 4, one or more recurring portions of the thread 20 can define a reference feature, or more specifically, a thread profile reference point, by which parameters of the thread 20 (such as thread pitch, for example) can be quantified or otherwise measured. For example, as depicted, one such thread profile reference point can be a "profile tangency point" 46 at the intersection between the distal relief surface 42 and the core 30 in the reference plane. The pitch of the thread 20 can be measured between the thread profile reference points 46 of longitudinally successive thread segments. Thus, the distal pitch P1 can be measured between the thread profile reference points 46 of longitudinally successive thread segments in the distal thread region 91. Another such thread profile reference point can be a "profile reference point" 48 at the intersection between a projection of the distal flank 38 and a projection of the core 30 in the reference plane. Other points along the thread profile can also be used as a thread profile reference point. A longitudinal distance X1 between the profile tangency point 46 of the distal relief surface 42 and a profile tangency point 47 of the distally adjacent proximal relief surface 44 can define a "core span" between thread segments in the reference plane.

Along each continuous portion of the thread 20, the thread profile reference point 46, 48 can be bound to a thread trajectory 50 of the bone screw 2. Stated differently, the reference point 46, 48 of each thread segment can be coincident with the thread trajectory 50. The thread trajectory 50 can thus define a reference diameter at each point along the helical thread path 32. In the illustrated embodiment, the reference diameter is a minor thread diameter.

It is to be appreciated that the thread profile geometry described above can be determined by the edge geometry of the cutting element(s) 80 of the thread-forming tool, such as a whirling tool, used to form the thread 20. On a CNC machine, such as a Swiss Lathe, for example, the cutting element(s) edge geometry can define a cutting edge reference point 81 (see FIG. 6) that corresponds to the profile tangency point 46 (or the profile reference point 48). The thread trajectory 50 can be communicated to the CNC machine, which can be programmed to control movement of the cutting element(s) in three-dimensional space with respect to the screw body 4 so that the cutting edge reference point 81 coincides with the thread trajectory 50 so as to form the thread 20.

A major thread diameter profile 60, as viewable in the reference plane, can also be defined for the bone screw 2, and can intersect the crest 36 of each uncropped thread segment. In the variable portion of the thread (i.e., intermediate thread region 93), where the thread flanks 38, 40 move closer together, cropped crests 36 may depart from the major thread diameter profile and move closer to the screw axis X, as shown in FIG. 5.

Figure 5:
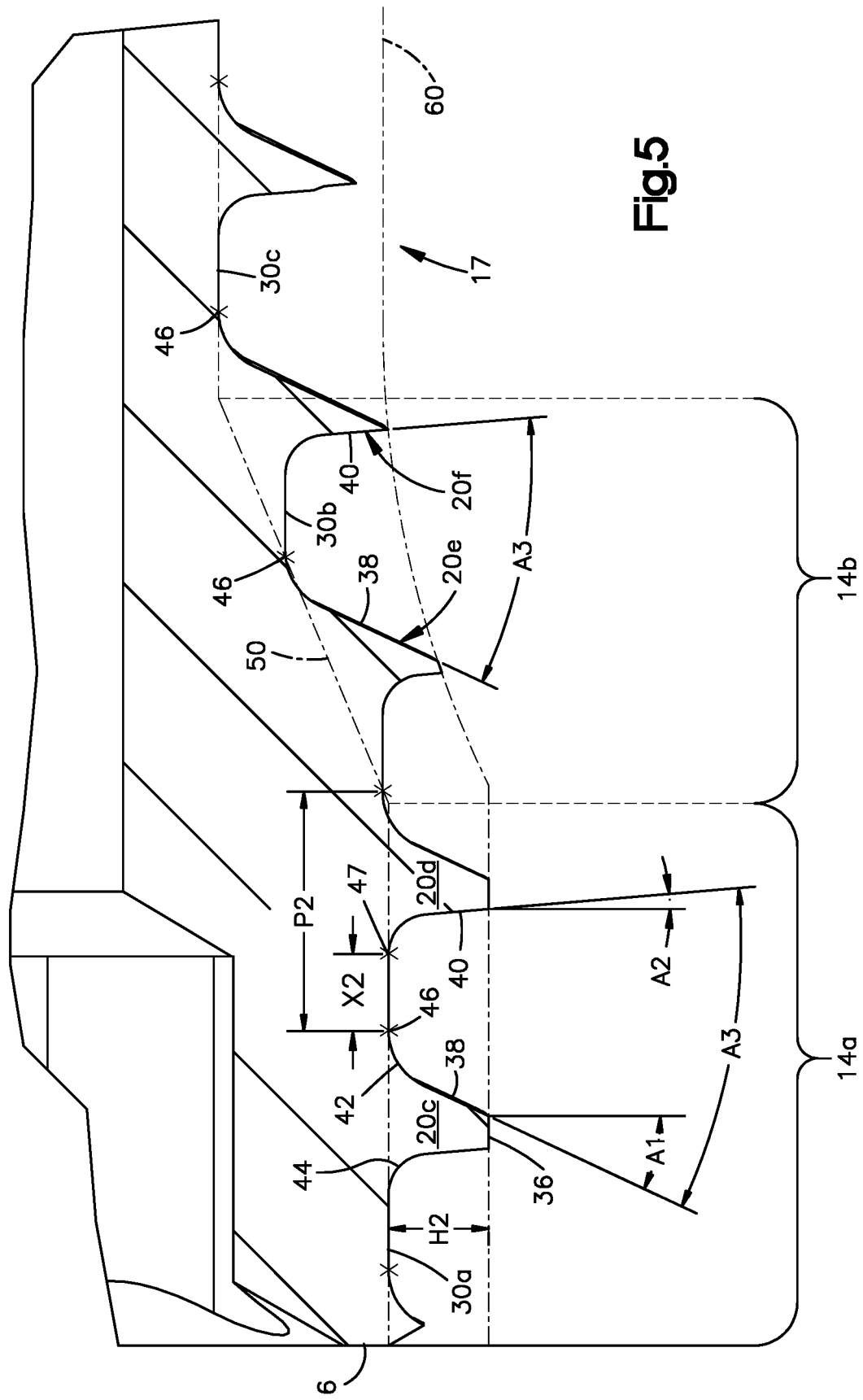
FIG. 5 is an enlarged, sectional view of a proximal portion of the thread along a head of the bone screw, taken along section line 4-4 as shown in FIG. 3.

Referring now to FIG. 5, the thread 20 at the proximal thread region 92 will now be described with reference to a pair of adjacent thread segments 20c, 20d of the main head portion 14a and a pair of adjacent thread segments 20e, 20f of the neck 14b. Even though these thread segments 20c-20f can be formed by a different thread-forming tool 82 (see FIG. 6) than that used to form the thread segments of the shaft 16 (such as distal shaft thread segments 20a, 20b described above), thread segments 20c-20f can define thread profiles generally similar to those of distal shaft thread segments 20a, 20b. However, a core span X2 in the proximal thread region 92 can be shorter than the core span X1 of the distal and intermediate thread regions 91, 93. This can be the result of thread forming tool 82 defining an associated cutting edge span shorter than that of the first thread-forming tool 81. As above, main head thread segments 20c, 20d and neck thread segments 20e, 20f can each include a root (i.e., the core 30), a crest 36, distal and proximal flanks 38, 40, and distal and proximal relief surfaces 42, 44. As above, the distal flanks 38 can have linear profiles whose orientations can be defined by the distal flank angle A1, the proximal flanks 40 can have linear profiles whose orientations can be defined by the proximal flank angle A2, and the distal flanks 38 can be offset from the proximal flanks 40 by the thread angle A3. In the proximal shaft region 92, the respective values of the distal flank angle A1, the proximal flank angle A2, and the thread angle A3 can be in the ranges listed above.

Preferably, the values of each of the distal flank angle A1, proximal flank angle A2, and thread angle A3 at the main head portion 14a and at the neck 14b are substantially equivalent to their respective values at the distal thread region 91. In other embodiments, one or more of these values can differ between the distal and proximal thread regions 91, 92. For example, the second cutting tool 82 used to form the thread in the proximal thread region 92 can define a different thread profile (including different flank angles, etc.) than that of the first cutting tool 80.

Also, as above, the proximal pitch P2 can be measured between the thread profile reference points 46 (or reference points 48) of longitudinally successive thread segments. The uncropped crests 36 at the main head portion 14a and neck 14b can define the major thread diameter profile 60 of the head 14.

As described above with reference to distal shaft thread segments 20a, 20b, the main head thread segments 20c, 20d and the neck thread segments 20e, 20f can each define thread profile reference points 46 and/or profile reference points 48 that are bounded to the thread trajectory 50 of the head 14. As above, one or both of reference points 46, 48 can correspond to an associated cutting edge reference point on the thread-forming tool used to form any of thread segments 20c-20f.

The main head thread segments 20c, 20d can define a primary thread height H2 measured radially from the head core 30a to the respective uncropped crest 36. The main head thread segments 20c, 20d can be truncated more so than the distal shaft thread segments 20a, 20b, for example, to reduce insertion torque. The primary thread height H2 of the main head thread segments 20c, 20d can be in a range of about 0.05 mm to about 1.00 mm. In other embodiments, primary thread height H2 can be in a range of about 0.15 mm to about 0.80 mm. In additional embodiments, primary thread height H2 can be about 0.15 mm to about 0.60 mm. It is to be appreciated that cropping, such as for forming the head cutting flutes 24, can reduce the height of the main head thread segments 20c, 20d, at least along a circumferential portion thereof.

In the reference plane, the neck thread segments 20e, 20f can be positioned relative to one another in step-like fashion. The distal flanks 38 of the neck thread segments 20e, 20f can have a radial dimension greater than that of the respective proximal flanks 40. A primary thread height each thread segment at the neck 14b can be quantified as an average of a first and second height measured from the uncropped crest 36, the first measured radially from the distal neck core 30b, and the second measured radially from the proximal neck core 30b. It is to be appreciated that the neck core 30b can be substantially parallel with the central axis X. In other embodiments, the neck core 30b can taper distally toward the central axis X.

Figure 6:
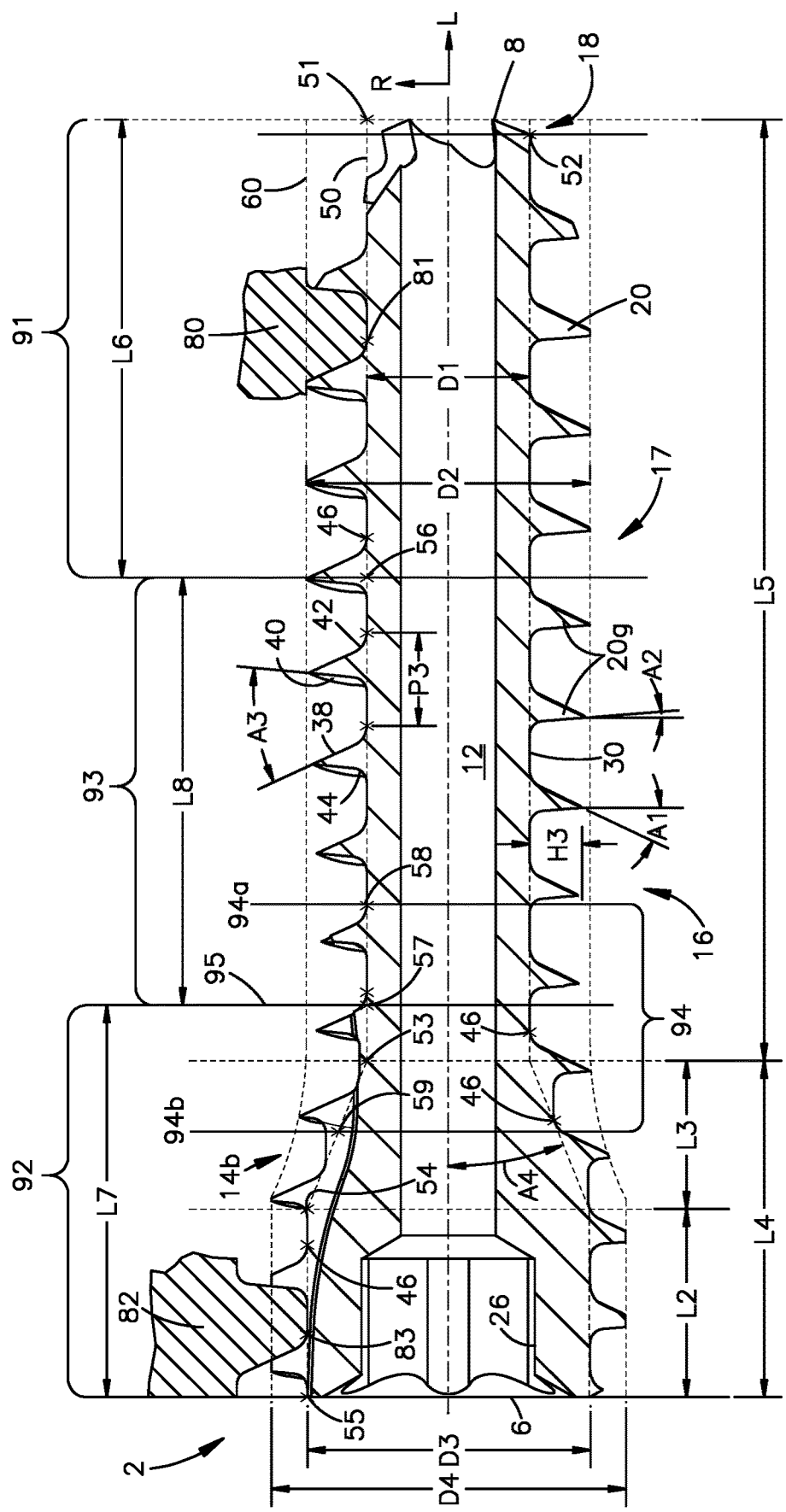
FIG. 6 is a sectional side view of the bone screw, taken along section line 4-4 as shown in FIG. 3.

Referring now to FIG. 6, at the intermediate thread region 91, intermediate thread segments 20g can define thread profiles generally similar to those of distal shaft thread segments 20a, 20b. For example, as above, thread segments 20g can each include a root (i.e., the core 30), a crest 36, distal and proximal flanks 38, 40, and distal and proximal relief surfaces 42, 44. As above, the distal flanks 38 can have linear profiles whose orientations can be defined by the distal flank angle A1, the proximal flanks 40 can have linear profiles whose orientations can be defined by the proximal flank angle A2, and the distal flanks 38 can be offset from the proximal flanks 40 by the thread angle A3. In the intermediate shaft region 93, the respective values of the distal flank angle A1, the proximal flank angle A2, and the thread angle A3 can be in the ranges listed above.

Preferably, the values of each of the distal flank angle A1, proximal flank angle A2, and thread angle A3 of the intermediate thread segments 20g are substantially equivalent to their respective values at the distal and/or proximal thread region 91, 92. In other embodiments, one or more of these values in the intermediate thread region 93 can differ with respect to those in the intermediate and/or proximal thread region 91, 92.

The intermediate pitch P3 can be calculated with reference to the thread profile reference points 46 (or profile reference points 48) bounded to the thread trajectory 50 in the intermediate thread region 93. In the illustrated embodiment, wherein the intermediate pitch P3 decreases proximally, the intermediate thread segments 20g can become cropped, such as by the thread-forming tool, which cropping can increase in the proximal direction. Thus, in the intermediate thread region 93, the thread height H3 (and thus the major thread diameter) can also decrease progressively in the proximal direction. As mentioned above, the cropped crests 36 of the intermediate thread segments 20g can drop radially inward from the major thread diameter profile 60.

To avoid cross-threading at the neck 14b, a thread transition zone 94 can be located at the boundary between the intermediate thread region 93 and the proximal thread region 91 (see also FIG. 3). The thread transition zone 94 can define a predetermined portion of the thread path 32 along which a tool transition occurs. In particular, along the thread transition zone 94, a first cutting tool 80 used to form the thread 20 in the distal and intermediate thread regions 91, 93 can disengage from the bone screw 2 and a second cutting tool 82 for forming the thread 20 in the proximal thread region 92 can engage the bone screw 2. The thread transition zone 94 can extend longitudinally from within the intermediate thread region 93 to a location within the proximal thread region 92, for example. The thread transition zone 94 can extend helically along the thread path 32 in a range of about 0 revolutions (i.e., the first cutting tool 80 disengages from the bone screw 2 immediately in the radial direction R away from the central axis X) to about 2.0 revolutions (i.e., about 720°) about the central axis X, and preferably within about 0.5 revolution (i.e., about 180°) about the central axis X.

Figure 7:
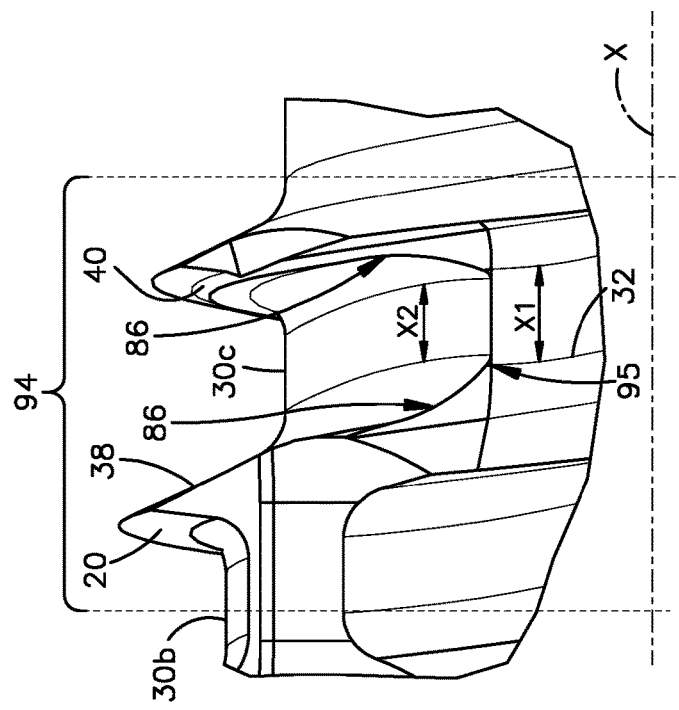
FIG. 7 is a perspective view of a thread transition location of the bone screw shown in FIGS. 1 through 6.

Referring now to FIG. 7, a predetermined transition location 95 can be located within the thread transition zone 94. The predetermined transition location 95 can coincide with (i.e., can define) the boundary between the intermediate thread region 93 and the proximal thread region 92. The predetermined transition location 95 can define a location with respect to the bone screw 2 at which an associated cutting edge reference point on the first cutting tool 80 begins moving radially away from the central axis X. The first cutting tool 80 can disengage from the body 4 of the bone screw 2 at a proximal end 94b of the thread transition region 94. Thus, the portion of the thread path 32 between the predetermined transition location 95 and the proximal end 94b of the thread transition region 94 can represent a withdrawal path of the first cutting tool 80. An associated cutting edge reference point 83 on the second cutting tool 82 preferably commences engagement with the body 4 (i.e., begins removing body 4 material so as to continue the thread 20) substantially at the predetermined transition location 95. As used herein with reference to engagement between the second cutting tool 82 and the body 4 of the screw 2, the term "substantially at the predetermined transition location" means within an axial tolerance of plus or minus (±) 6% of the proximal pitch P2 and an angular tolerance of plus or minus (±) 20° of the predetermined transition location 95

The second cutting tool 82 can optionally begin moving radially towards the central axis X once the cutting edge reference point of the second cutting tool 82 reaches the distal end 94a of the transition region 94. Additionally, the first cutting tool 80 can transition from the decreasing intermediate pitch P3 to the constant proximal pitch P2 (such as by "leveling off" its rate of proximal advancement relative to the bone screw 2) from the distal end 94a of the thread transition zone 94 to the predetermined transition location 95, for example.

As shown, the core span X2 along the thread path 32 between the predetermined transition location 95 and the proximal end 6 can be shorter than the core span X1 along the thread path 32 between the predetermined transition location 95 and the distal end 8. The shorter span X2 can help avoid cross-threading at the head 14. The shorter span X2, combined with keeping angles A1, A2, and A3 substantially the same, can prevent the second cutting tool 82 from cutting into the thread flanks 38, 40 defined by the first cutting tool 80 during its withdrawal. However, the shorter span X2 can form steps 86 in the distal and proximal flanks 38, 40 on either side of the predetermined transition location 95. The transition zone 94 will be discussed in more detail below.

Referring again to FIG. 6, the bounds of some of the foregoing components and features of the bone screw 2 can be at least partially defined by the thread trajectory 50. For example, the distal end 8 of the bone screw 2, as well as a distal boundary of the distal thread region 91, can coincide with a first core reference location 51 on the thread trajectory 50. The tip portion 18 of the shaft 16 can extend proximally from the first core reference location 51 to a second core reference location 52 on the thread trajectory 50.

The main shaft portion 17 can extend proximally from the second core reference location 52 to a third core reference location 53 on the thread trajectory 50. The neck 14b can extend proximally from the third core reference location 53 to a fourth core reference location 54 on the thread trajectory 50. The main head portion 14a can extend proximally from the fourth core reference location 54 to a fifth core reference location 55. The fifth core reference location 55 preferably coincides with the proximal end 6 of the bone screw 2. The first through fifth reference locations 51-55 can generally define parameters of the core 30 (and thus parameters of the minor thread diameter of the bone screw 2).

A sixth core reference location 56 on the thread trajectory 50 can define the boundary between the distal and intermediate thread regions 91, 93. The sixth core reference location 56 can be located longitudinally intermediate the second and third core reference locations 52, 53. A seventh core reference location 57 on the thread trajectory 50 can define the boundary between the intermediate and proximal thread regions 93, 92, and thus can also define the predetermined transition location 95. An eighth core reference location 58 and a ninth core reference location 59 on the thread trajectory 50 can define distal and proximal boundaries of the thread transition zone 94. The sixth through ninth reference locations 56-59 can generally define parameters of the thread 20 (and thus parameters of the major thread diameter of the bone screw 2).

In embodiments where the bone screw 2 has a total of two thread regions 91, 92, the sixth core reference location 56 can be omitted or disregarded, and the distal and proximal thread regions 91, 92 can share a border located at the seventh core reference location 57. In embodiments where the bone screw 2 has a single thread region 91, the sixth core reference location 56 can be omitted or disregarded, and the seventh core reference location 57 can define the predetermined transition location.

The total length L1 of the bone screw 2 can be defined longitudinally between the first and fifth core reference locations 51, 55 (i.e., between the distal and proximal ends 8, 6). The length L1 of the bone screw 2 can be in a range of about 8 mm to about 60 mm. In other embodiments, the length L1 of the bone screw 2 can be less than 8 mm. In additional embodiments, the length L1 of the bone screw 2 can be greater than 60 mm, such as in a range of about 60 mm to about 200 mm. The length L1 of the bone screw 2 can be, by way of non-limiting examples, any one of: less than about 8 mm; about 8 mm; about 10 mm; about 12 mm; about 14 mm; about 16 mm; about 18 mm; about 20 mm; about 22 mm; about 24 mm; about 26 mm; about 28 mm; about 30 mm; about 32 mm; about 34 mm; about 36 mm; about 38 mm; about 40 mm; about 42 mm; about 44 mm; about 46 mm; about 48 mm; about 50 mm; about 52 mm; about 54 mm; about 56 mm; about 58 mm; about 60 mm, about 65 mm, about 70 mm, about 75 mm, about 80 mm, about 85 mm, about 90 mm, about 95 mm, about 100 mm, about 105 mm, about 110 mm, about 115 mm, about 120 mm, about 125 mm, about 130 mm, about 135 mm, about 140 mm, about 145 mm, about 150 mm, about 155 mm, about 160 mm, about 165 mm, about 170 mm, about 175 mm, about 180 mm, about 185 mm, about 190 mm, about 195 mm, about 200 mm, or any length between any of the foregoing lengths.

A length L2 of the main head portion 14a can be defined longitudinally between the fourth and fifth core reference locations 54, 55. The main head length L2 can be in a range of about 1.00 mm to about 8.00 mm. In other embodiments, the main head length L2 can be in a range of about 2.00 mm to about 3.50 mm. In additional embodiments, the main head length L2 can be in a range of about 2.30 mm to about 2.80 mm.

A length L3 of the neck 14b can be defined longitudinally between the third and fourth core reference locations 53, 54. The neck length L3 can be in a range of about 1.00 mm to about 4.00 mm. In other embodiments, the neck length L3 can be in a range of about 1.50 mm to about 2.50 mm. In additional embodiments, the neck length L3 can be in a range of about 2.00 mm to about 2.30 mm.

A taper angle A4 of the neck 14b can be defined as the slope of the thread trajectory 50 at the neck 14b (i.e., between the third and fourth core reference locations 53, 54) with respect to the central axis X. The neck taper angle A4 can be in a range of about 5° to about 45°. In other embodiments, the neck taper angle A4 can be in a range of about 10° to about 30°. In additional embodiments, the neck taper angle A4 can be in a range of about 13° to about 23°. In other embodiments, the neck 14b can taper along a curve (i.e., the thread trajectory 50 at the neck 14b can be curved). In such embodiments, the neck taper angle A4 can be quantified as the slope of a straight reference line intersecting the fourth and third core reference locations 54, 53, measured with respect to the central axis X.

A total length L4 of the head 14 can be defined longitudinally between the third and fifth core reference locations 53, 55. The total length L4 of the head 14 can be the sum of L2 and L3 (L4=L2+L3).

A length L5 of the shaft 16 can be defined longitudinally between the first and third core reference locations 51, 53. The shaft length L5 can be about 6.0 mm or less. In other embodiments, the shaft length L5 can be in a range of about 6.0 mm to about 198 mm. In additional embodiments, the shaft length L5 can be in a range of about 6.0 mm to about 58.0 mm.

A ratio of the main head length L2 to the total length L1 of the screw body 2 can be in a range of about 0.010:1 to about 0.350:1. This ratio can decrease within the foregoing range as the total screw length L1 increases and can increase within the foregoing range as the total screw length L1 decreases.

A ratio of the total length L4 of the head 14 to the total length L1 of the screw body 2 can be in a range of about 0.013:1 to about 0.60:1. As above, this ratio can decrease within the foregoing range as the total screw length L1 increases and can increase within the foregoing range as the total screw length L1 decreases.

A total length L6 of the distal thread region 91 can be defined longitudinally between the first and sixth core reference locations 51, 56. The total length L6 of the distal thread region 91 can be at least about 5% of the total length L1 of the bone screw 2. In embodiments where the bone screw 2 has three thread regions 91, 92, 93, the total length L6 of the distal thread region 91 can extend up to about 50% of the total length L1 of the bone screw 2, more particularly up to about 33.3% of the total length L1 of the bone screw 2, and preferably about 20% of the total length L1 of the bone screw 2. In embodiments where the bones screw 2 has a total of two thread regions 91, 92, the total length L6 of the distal thread region 91 can be from about 5% to about 95% of the total length L1 of the bone screw 2.

A total length L7 of the proximal thread region 92 can be defined longitudinally between the seventh and fifth core reference locations 57, 55. The total length L7 of the proximal thread region 92 can be at least equivalent to, and preferably greater than, the total length L5 of the head 14. In additional embodiments, however, the total length L7 of the proximal thread region 92 can be less than the total length L5 of the head 14. In embodiments where the bones screw 2 has a total of two thread regions 91, 92, the total length L7 of the proximal thread region 92 can be from about 5% to about 95% of the total length L1 of the bone screw 2.

A total length L8 of the intermediate thread region 93 can be defined longitudinally between the sixth and seventh core reference locations 56, 57. Thus, the length L8 of the intermediate thread region 93 can be the difference between the total length L1 of the bone screw 2 and the sum of the total lengths L6, L7 of the distal and proximal thread regions 91, 92 (L8=L1−L6−L7).

The main shaft portion 17 can define a shaft minor thread diameter D1 in a range of about 1.00 mm to about 7.50 mm. In other embodiments, minor diameter D1 can be in a range of about 1.25 mm to about 3.5 mm. In additional embodiments, minor thread diameter D1 can be in a range of about 1.50 mm to about 2.50 mm.

In the distal thread region 91, the main shaft portion 17 can define a shaft major thread diameter D2 in a range of about 1.10 mm to about 8.0 mm. In other embodiments, major thread diameter D2 can be in a range of about 1.50 mm to about 5.00 mm. In additional embodiments, major thread diameter D2 can be in a range of about 1.80 mm to about 4.10 mm.

The main head portion 14a defines a main head minor thread diameter D3 in a range of about 1.40 mm to about 9.0 mm. In other embodiments, the minor thread diameter D3 can be in a range of about 2.50 mm to about 5.00 mm. In additional embodiments, minor thread diameter D3 can be in a range of about 3.00 mm to about 4.00 mm.

The main head portion 14a defines a main head major thread diameter D4 in a range of about 1.45 mm to about 13.5 mm. In other embodiments, the minor thread diameter D3 can be in a range of about 2.5 mm to about 6.50 mm. In additional embodiments, minor thread diameter D3 can be in a range of about 3.0 mm to about 5.50 mm.

It is to be appreciated that any of the foregoing diameters D1, D2, D3, D4 can be substantially constant over the length of their respective component of the bone screw 2. Thus, the shaft minor thread diameter D1 can be substantially constant over the shaft length L5 (minus the length of the tip portion 18). Stated differently, the main shaft core 30c can extend parallel with the central axis X. The shaft major thread diameter D2 can be substantially constant over the length L6 of the distal shaft portion 91 (minus the length of the tip portion 18). The main head minor thread diameter D3 can be substantially constant over the entire main head length L2. Stated differently, the main head core 30a can extend parallel with the central axis X. The main head major shaft diameter D4 can be substantially constant over the entire main head length L2.

In other embodiments, one or both of the main shaft core 30c and the main head core 30a can have different diameters at various longitudinal locations thereof. For example, one or both of the main shaft core 30c and the main head core 30a can taper with respect to the central axis X up to a taper angle of about 10°, or can have a portion with a curved profile in the reference plane. In such embodiments, foregoing diameters D1, D2, D3, D4 can be measured at any portion of the respective component of the bone screw 2. Moreover, in such embodiments, diameters D1, D2, D3, D4 can be an average diameter of the respective component along its length. It is to be appreciated that any of the foregoing diameters D1, D2, D3, D4, whether a constant diameter or an average diameter, can be referred to as a respective "diameter value."

A ratio of the main head minor thread diameter D3 to the main shaft minor thread diameter D1 can be in a range of about 1.10:1 to about 3.00:1. In other embodiments, the ratio of the main head minor thread diameter D3 to the main shaft minor thread diameter D1 can be in a range of about 1.25:1 to about 2.00:1. In additional embodiments, the ratio of the main head minor thread diameter D3 to the main shaft minor thread diameter D1 can be in a range of about 1.50:1 and about 1.80:1.

A ratio of the main head major thread diameter D4 to the main shaft major thread diameter D2 can be in a range of about 1:1 to about 2.25:1. In other embodiments, the ratio of the main head major thread diameter D4 to the main shaft major thread diameter D2 can be in a range of about 1.10:1 to about 1.30:1. In additional embodiments, the ratio of the main head major thread diameter D4 to the main shaft major thread diameter D2 can be in a range of about 1.15:1 and about 1.80:1.

In one non-limiting example embodiment, the bone screw 2 has a total length L1 of about 50 mm, a main head length L2 of about 2.4 mm, and a total head length L4 of about 4.6 mm, a neck taper angle A4 of about 14°. In this embodiment, the bone screw 2 defines the distal, proximal, and intermediate thread regions 91, 92, 93. The distal flank angle A1 is about 25°, the proximal flank angle A2 is about 5°, and the thread angle A3 is about 30°, and each of these angles A1, A2, A3 is substantially constant along each of the thread regions 91, 92, 93. The distal thread region 91 extends proximally from the distal end 8 of the bone screw 2 to a length L6 of about 10 mm and defines a distal pitch P1 of about 1.22 mm. The proximal thread region 92 extends distally from the proximal end 6 of the bone screw 2 to the predetermined transition location 95 at a length L7 of about 5.50 mm and defines a proximal pitch P2 of about 1.08 mm. The intermediate thread region 93 extends proximally from a shared boundary with the distal thread region 91 to a shared boundary with the proximal thread region 91 (i.e., the predetermined transition location 95) at a length L8 of about 34.5 mm. The intermediate pitch P3 decreases at a substantially constant rate from P1 at its shared boundary with the distal thread region 91 to P2 at its shared boundary with the proximal thread region 92. The main head portion 14a defines a minor thread diameter D3 of about 3.0 mm and a major thread diameter D4 of about 3.6 mm. The main shaft portion 17 defines a minor thread diameter D1 of about 1.9 mm and a major thread diameter D2 (in the distal thread region 91) of about 3.0 mm. In this exemplary embodiment, the ratio of the distal pitch P1 to the proximal pitch P2 is about 1.130; the ratio of the main head length L2 to the total screw length L1 is about 0.048:1; the ratio of the total head length L4 to the total screw length L1 is about 0.092:1; the ratio of the main head minor thread diameter D3 to the main shaft minor thread diameter D1 is about 1.579:1; and the ratio of the main head major thread diameter D4 to the main shaft major thread diameter D2 is about 1.200:1.

It is to be appreciated that the dimensions of the bone screws 2 disclosed herein represent non-limiting examples of the sizes, shapes, and orientations of the bone screws 2 and their components. Furthermore, the bone screws 2 can be scaled to sizes that are larger or smaller than those disclosed herein without departing from the scope of the embodiments of the present disclosure.

Figure 8:
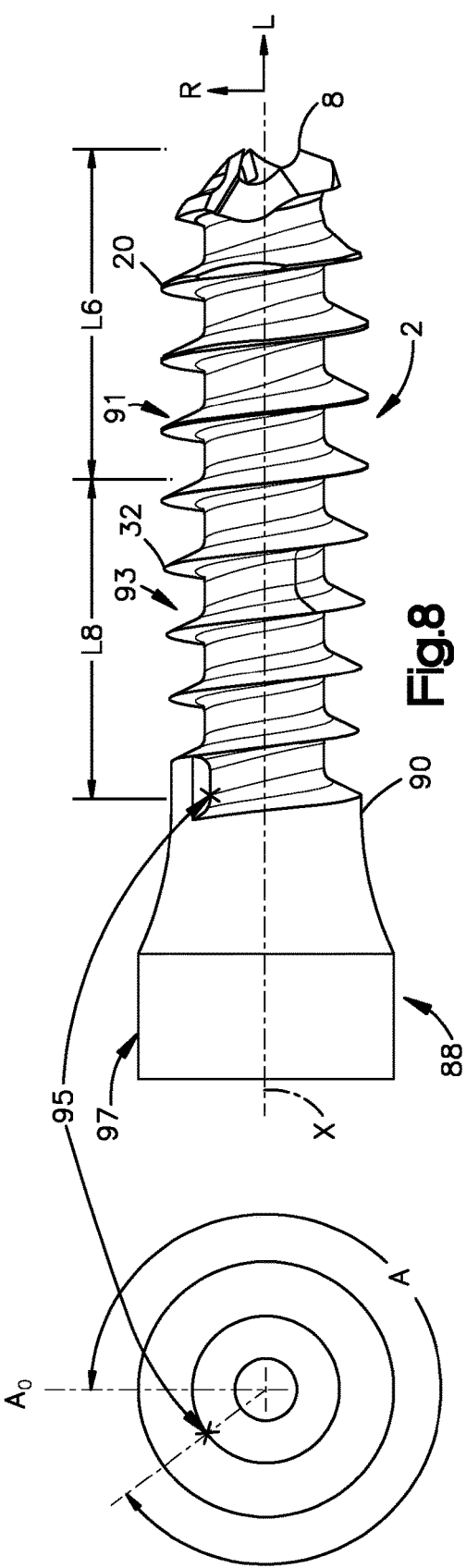
FIG. 8 shows orthogonal views of a bone screw in an intermediate configuration of a thread-forming process, showing longitudinal and angular positions of the thread transition location shown in FIG. 7.

With reference to FIG. 8, formulas for precisely identifying the predetermined transition location 95 with respect to the longitudinal direction L and an angular position A about the central axis X will now be described. The inventor found through her own testing that to manufacture the bone screws 2 described above (i.e., with a pitch transition location 95 at or near a head 14 (or a neck 14b thereof)) with an automated thread-forming device (such as a Swiss lathe), the device requires new programming to execute the tool transition described above to avoid cross-threading (or at least to reduce cross-threading to within acceptable limits). For such programmability, the predetermined transition location 95 must be precisely identified with respect to L and A. Because the bone screws 2 described above can be sized, shaped, and otherwise configured according to a wide range of parameter values, providing a single set of equations for calculating the precise location of the transition location 95 in at least 2D space requires consideration of a number of parameters, including the following parameters:

L6: length of the distal thread portion 91;
L8: length of the intermediate thread portion 93;
P1: thread pitch of the distal thread region 91;
P2: thread pitch of the proximal thread region 92;
K: constant rate of pitch change per revolution ("N") of the lathe spindle of the thread-forming tool;
N: total number of revolutions of the spindle relative to the bone screw 2.

When the distal thread portion 91 extends at a constant pitch P1 along L6 from the distal end 8 to a shared boundary with the intermediate portion 93, and the intermediate portion 93 extends to the predetermined transition location 95 at a pitch P3 that decreases at constant rate K along L8, the total number of revolutions N of the spindle from the distal end 8 to the predetermined transition location 95 can be expressed by the following equation:

$$N = \frac{2*L8}{P1+P2} + \frac{L6}{P1}. \qquad \text{Equation 1}$$

In Equation 1, N=0 when the cutting edge reference point of the thread-forming tool is coincident with the distal end 8 of the bone screw 2. Equation 1 also utilizes the following substitution for K constant over the intermediate thread portion 93:

$$K = \frac{P2-P1}{N_{93}}, \qquad \text{Equation 2}$$

as defined in G-code program function G34 X Z F K (variable pitch threading) on a Citizen L20-XII Swiss lathe, manufactured by Citizen Machinery UK Ltd, based in Bushey, United Kingdom.

The general function for pitch with respect to screw rotation is linear:

$$P(n)=P1+K*n. \qquad \text{Equation 3}$$

For a portion of the bone screw having a constant pitch (such as distal thread portion 91 having constant distal pitch P1 over length L6), the length l of such portion is a function of the pitch P and number of revolutions n:

$$l=P*n. \qquad \text{Equation 4}$$

For the distal thread region 91, the revolutions n can be solved as follows:

$$N_{91} = \frac{L6}{P1}. \qquad \text{Equation 5}$$

The derivative of Equation 4 can be used for other thread sections for calculating length as a function of pitch:

$$dl=P*dn. \qquad \text{Equation 6}$$

However, for a portion of the bone screw 2 having a variable pitch (such as intermediate thread portion 93 with length L8), Equation 3 can be substituted for P in Equation 6, as shown in Equation 7 below:

$$dl=(P1+K*n)dn, \qquad \text{Equation 7}$$

which can be derived over the revolutions n in the variable pitch section as follows:

$$l=\int_{n=0}^{N_{93}}(P1+K*n)dn, \qquad \text{Equation 8}$$

which can be integrated as follows:

$$l = K\left(\frac{n^2}{2}\right) + P1*n + C. \qquad \text{Equation 9}$$

Constant C can be calculated to be C=0 at the starting point (n=0, l=0) of the intermediate thread portion 93. With the constant C defined (C=0), the length l over the intermediate thread portion 93 (L8) can be expressed as follows:

$$l = K\left(\frac{n^2}{2}\right) + P1*n. \qquad \text{Equation 10}$$

Equation 2 can be substituted for K in Equation 10, which can then be solved for l=L8 at the end point n=$N_{93}$ as shown in Equation 11 below:

$$L8 = \left(\frac{P2-P1}{N_{93}}\right)\left(\frac{N_{93}^2}{2}\right) + P1*N_{93}, \qquad \text{Equation 11}$$

which can be solved for $N_{93}$ as follows:

$$N_{93} = \frac{2*L8}{P1+P2}. \qquad \text{Equation 12}$$

Thus, the total number of revolutions N from the distal end 8 to the predetermined transition location 95, as found in Equation 1, can be calculated as the sum of Equations 5 and 12.

The angular position A of the spindle at the predetermined transition location 95 can be calculated as follows:

$$A=(N-|N|)\times 360°. \qquad \text{Equation 13}$$

Thus, for the exemplary embodiment described above (L6=10.0 mm; P1=1.22 mm; L8=34.5 mm; P2=1.08 mm), the spindle of the thread-forming device will rotate a total number of N=38.197 revolutions, which equates to an angular position of A=70.92° according to Equation 13. Thus, with pitches P1, P2 and the respective lengths L6, L8 of the distal and intermediate thread portions 91, 93 defined, the foregoing equations can be employed to program a CNC thread-forming device, such as a Swiss lathe, to cause the cutting element of the thread-forming tool (such as a whirling tool), to begin moving away from the central axis X along the helical path 32 once the spindle rotates the bone screw 2 at the predetermined number of revolutions N and angular position A with respect to the cutting edge reference point of the tool.

An example method of forming, shaping, or otherwise preparing a bone screw 2 with an automated thread-forming device will now be described.

During a first, preforming step, one or more predetermined bone screw 2 geometries can be pre-programmed into a control unit, such as a CNC unit, that defines a coordinate system in three-dimensional space and is in electrical communication with the automated thread-forming device so as to be capable of controlling cutting tools of the device in three-dimensional space for shaping the bone screw 2 according to the one or more predetermined bone screw 2 geometries. Such predetermined bone screw geometries 2 can include any of those described above. In addition, any of and up to all of the first through ninth core reference locations 51-59 can be pre-programmed as coordinates of respective ones of one or more predetermined bone screws 2.

During a second, preforming step, an operator can select at least one of the one or more predetermined bone screw 2 geometries for manufacture. A plurality of screw blanks (also referred to as "stocks"), optionally of various lengths, can be pre-loaded into one or more magazines of the automated thread forming device. In such embodiments, the second step can include selecting a screw blank from the plurality of screw blanks to be manufactured into a bone screw 2 defining one of the selected predetermined bone screw 2 geometries. The automated thread-forming device can autonomously perform the blank selection step via performing a sub-step of comparing the at least one of the one or more predetermined bone screw 2 geometries with the pre-defined geometries of the pre-loaded screw blanks.

During a third step, a proximal portion 97 of a screw blank 88, such as the selected screw blank from step 2, can be loaded into a chuck that is rotatably fixed to a spindle, such as a front spindle, of the device.

During a fourth step, one or more first cutting tools can engage (i.e., remove blank material from) the blank 88 along a central axis X of the blank 88 so as to form the cannulation 12. The blank 88 can optionally be transferred to a back spindle before, during, or after this step.

During a fifth step, one or more second cutting tools can engage the proximal end 6 of the blank 88 to form the socket 26. This step can occur while the blank 88 is affixed to the back spindle. This step can also include a step of transferring the blank 88 to the back spindle.

During a sixth step, with the proximal portion 97 of the blank 88 attached to the front spindle, one or more third cutting tools can engage the blank 88 between the first core reference location 51 (i.e., the distal end 8) and the second core reference location 52 to pre-form the tip portion 18, including, e.g., an optional tip chamfer. This step can include transferring the blank 88 from the back spindle to the front spindle.

During a seventh step, one or more fourth cutting tools can engage a distal portion of the blank 88, including the tip portion 18, to form one or more distal cutting flutes 22, one or more cutting teeth 23, and associated relief surfaces, which can be configured as more fully described in the Zastrozna Reference.

During an eighth step, a fifth cutting tool, such as a whirling tool 80, can commence engaging the distal end 8 of the blank 88 with the cutting edge reference point 81 of the whirling tool 80 coinciding with the first core reference location 51 of the blank 88. The first core reference location 51 can be defined within the coordinate system as an angular coordinate associated with a relative rotational position of $N=0$ revolutions of the front spindle ($A=A_0=0$) (and thus also of the blank 88) with respect to the first cutting tool 80 about the central axis X. The first core reference location 51 can also be defined within the coordinate system as a first axial coordinate associated with a relative axial position of length $l=0.00$ mm between the first cutting tool 80 and the blank 88 along the central axis X. The first core reference location 51 can also be defined within the coordinate system as a second axial coordinate along a second axis perpendicular to the central axis X (i.e., the second axis being oriented along the radial direction R), which second axial coordinate is associated with a radial distance between the first cutting tool 80 and the central axis X. In this manner, the angular coordinate and the first and second axial coordinates can define the first core reference location 51 in the three-dimensional space of the coordinate system. It is to be appreciated that any of and up to each of core reference locations 51-59 can be defined within the coordinate system as a respective angular coordinate about the central axis X, a respective first axial coordinate along the central axis, and a respective second axial coordinate along the second axis.

During a ninth step, the front spindle can then be rotated with respect to the whirling tool 80 as at least one of the blank 88 and the whirling tool 80 is translated longitudinally with respect to the other at a first, constant speed along length L6, thereby causing the whirling tool 80 to form the thread 20 along the helical thread path 32, including along the one or more teeth 23, as the whirling tool 80 advances proximally with respect to the blank 88. This causes the whirling tool 80 to engage an exterior 90 of the blank 88 along the helical thread path 32, thereby forming the thread 20 in the distal thread region 91 having constant distal pitch P1. The constant translational speed can be maintained until the cutting edge reference point 81 of the whirling tool 80 coincides with the sixth core reference location 56.

During a tenth step, once the cutting edge reference point 81 reaches the sixth core reference location 56 (i.e., the boundary between the distal and intermediate thread regions 91, 93), the relative translational speed between the whirling tool 80 and the blank 88 can be increased at a constant rate K along length L8 to the seventh core reference location 57, thereby forming the thread 20 in the intermediate thread region 93 having variable pitch P3.

During an eleventh step, once the cutting edge reference point 81 reaches the eighth core reference location 58 (i.e., the distal boundary 94a of the thread transition zone 94) a sixth cutting tool 82 can approach the exterior 90 of the blank 88 along the thread path 32. The second cutting tool 82 can be another whirling tool or other multi-cutting element tool, or can alternatively be a single-cutting element tool.

During a twelfth step, once the CNC unit identifies that the cutting edge reference point 81 of the whirling tool 80 reaches the predetermined transition location 95 (i.e., the reference point 81 coincides with the first axial coordinate and the angular coordinate associated with the predetermined transition location 95), the whirling tool 80 can begin withdrawing from the exterior 90 of the blank 88 (i.e., increasing the radial distance between the cutting edge reference point 81 and the central axis X) along the withdrawal path. A processor of the CNC unit can derive the first axial coordinate and the angular coordinate associated with the predetermined transition location 95 via executing one or more algorithms or equations, including the equations set forth above. The whirling tool 80 can disengage from the blank 88 when the cutting edge reference point 81 of the whirling tool 80 reaches the ninth core reference location 59 (i.e., the proximal end 94b of the thread transition region 94). Preferably, synchronously with the whirling tool 80 withdrawing from the blank 88 along the thread transition zone 94, the sixth cutting tool 82 can commence engaging the exterior 90 of the blank 88 when the cutting edge reference point 83 of the sixth cutting tool 82 substantially coincides with the predetermined transition location 95 (i.e., at the seventh core reference location 57 and angular position A). It is to be appreciated, however, that the sixth cutting tool 82 can commence engaging the exterior 90 of the blank 88 after the whirling tool 80 has disengaged the blank 88.

During a thirteenth step, once the cutting edge reference point 83 of the sixth cutting tool 82 engages the exterior 90 of the blank 88 at the predetermined transition location 95 (i.e., the reference point 83 coincides with the first axial coordinate and the angular coordinate associated with the predetermined transition location 95), the relative translational speed between the blank 88 and the sixth cutting tool 82 can be maintained at a constant speed as the cutting edge reference point 83 of the sixth cutting tool 82 advances proximally to the third core reference point 53, thereby forming the thread 20 in the proximal thread region 92 having constant proximal pitch P2.

During a fourteenth step, once the cutting edge reference point 83 of the sixth cutting tool 82 coincides with the third core reference location 53, the radial distance between the cutting edge reference point 83 and the central axis X can be increased from the third core reference location 53 to the fourth core reference location 54 such that the cutting edge reference point 83 sweeps along the thread trajectory 50 of the neck 14b, and while the translational speed is maintained constant, thereby causing the sixth cutting tool 82 to form the thread 20 along the helical thread path 32 along the neck 14b at proximal pitch P2.

During a fifteenth step, once the cutting edge reference point 83 of the sixth cutting tool 82 coincides with the fourth core reference location 54, the radial distance between the cutting edge reference point 83 and the central axis X can be maintained, along with the constant translational speed, as the cutting edge reference location advances proximally to the fifth core reference location 55 (i.e., the proximal end 6 of the bone screw). Thus, the main head portion 14a can be formed having a substantially constant minor thread diameter D2.

As mentioned above, the core 30 of one or both of the main shaft portion 17 and the main head portion 14a can define a taper with respect to the central axis X. In such embodiments, the radial distance between the respective cutting edge reference point 81, 83 and the central axis X can be increased as necessary during the associated step(s) to define the taper.

During a sixteenth step, one or more seventh cutting tools can engage the proximal portion 97 of the blank 88 to form the one or more head cutting flutes 24.

During a seventeenth step, the proximal end 6 of the bone screw 2 can be severed from a proximal portion 97 of the blank 88. The proximal end 6 can be further machined, such as by planarizing and/or polishing the proximal-most surface 7, for example.

It is to be appreciated that at least one of the one or more first, second, third, fourth, and seventh cutting tools described above can be used in more than one of the foregoing third, fourth, fifth, sixth, seventh, sixteenth, and seventeenth steps.

It is also to be appreciated that one or more of the foregoing first through seventeenth steps can be performed in a different sequence with respect to at least one other of these steps.

Figure 9:
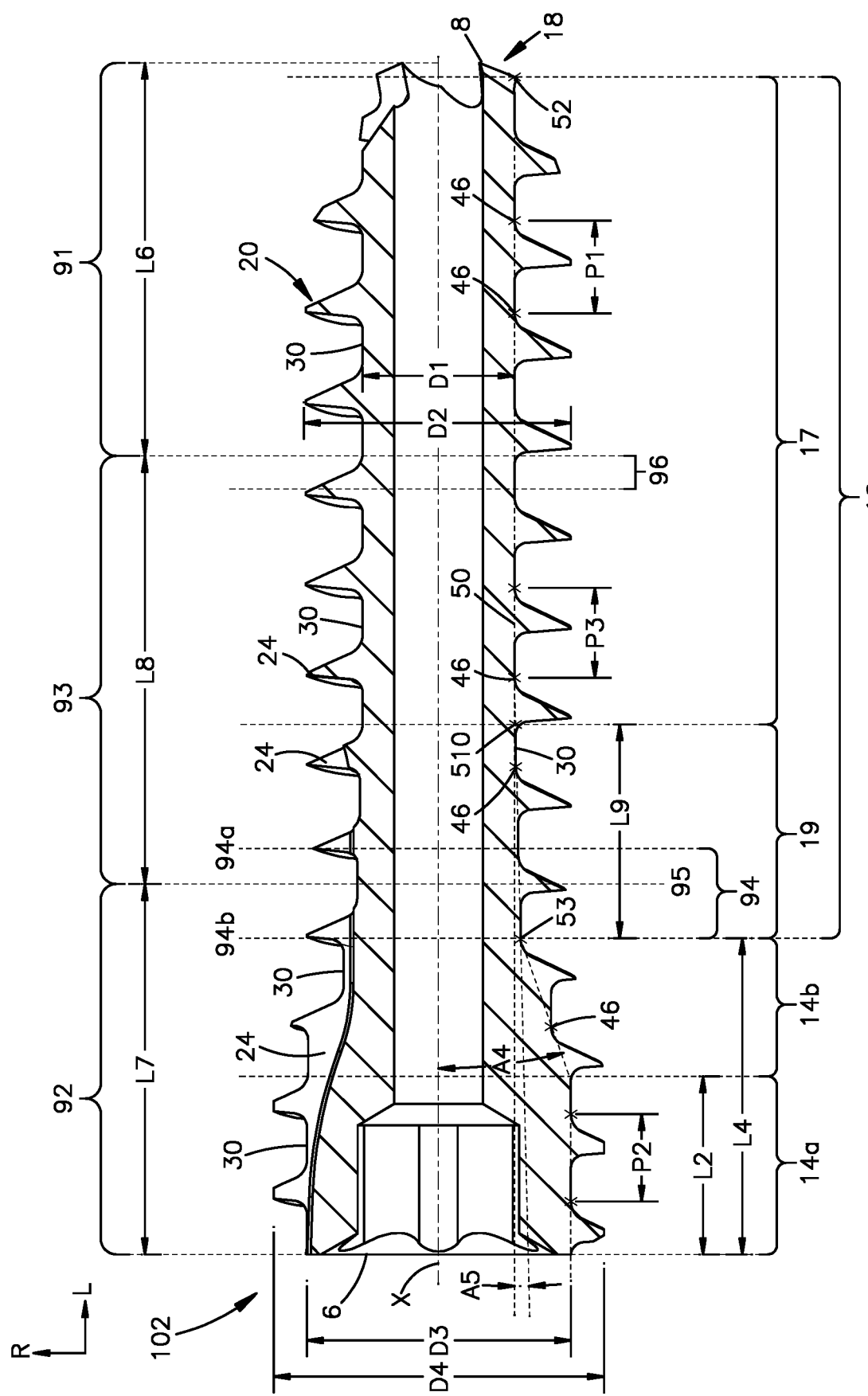
FIG. 9 is a sectional side view of a bone screw, according to another embodiment of the present disclosure.

Referring now to FIG. 9, another embodiment of a bone screw 102 is shown, which can be configured similarly to the bone screw 2 described above. For the sake of brevity, the following discussion will focus on the differences between bone screw 102 and bone screw 2.

In the present embodiment, the shaft 16 can include a tapered portion 19 extending longitudinally between the neck 14b and the main shaft portion 17. A taper angle A5 of the tapered shaft portion 19 can be defined as the slope of the thread trajectory 50 at the tapered shaft portion 19 with respect to the central axis X. Taper angle A5 can be in a range of about 10° or less. In other embodiments, taper angle A5 can be in a range of about 5° or less. In additional embodiments, the taper angle A5 can be less than 1°. The tapered shaft portion 19 can increase the torsional strength of the bone screw 102, such as by reducing stress concentrations between the neck 14b and the shaft 16, for example, while only marginally increasing the insertion torque. The head flute(s) 24 can also be elongated distally to reduce insertion torque.

The thread profile along the tapered shaft portion 19 can be similar and even substantially equivalent to the thread profile along the main shaft portion 17. As above, the thread 20 along the tapered shaft portion 19 can define reference points 46 along which the thread trajectory 50 extends, as viewed in the reference plane. The core 30 in the tapered shaft portion 19 can be parallel with the central axis X so that, in the reference plane, the core can rise proximally in step-like fashion.

The tapered shaft portion 19 can extend proximally from a tenth core reference location 510 on the thread trajectory 50 to the third core reference location 53. Thus, the tapered shaft portion 19 can have a length L9 measured longitudinally between the tenth and third reference locations 510, 53. In such embodiments, the main shaft portion 17 can extend proximally from the second core reference location 52 to the tenth core reference location 510. The length L9 of the tapered shaft portion 19 can be about 1.0 mm or greater. In some embodiments, length L9 can be about 5.0 mm or greater. In some embodiments, the tapered shaft portion 19 can extend distally to the tip portion 18 (i.e., the entire shaft 16 can be tapered, as described above). The predetermined transition location 95, and thus at least a portion of the thread transition zone 94, can be located on the tapered portion 19 of the shaft 16.

Similarly as described above, the bone screw 102 can define a distal thread region 91 having a distal pitch P1, a proximal thread region 92 having a proximal pitch P2, and an intermediate thread region 93 having an intermediate pitch P3. As above, the distal pitch P1 can be constant, and the proximal pitch P2 can be constant and can be less than the distal pitch P1. In the present embodiment, the intermediate pitch P3 can be substantially constant, and can be less than P1 and can be greater than P2. Accordingly, a second thread transition zone 96 can extend proximally from the boundary between the distal and intermediate thread regions 91, 93, wherein the thread 20 can transition from the distal pitch P1 to the intermediate pitch P1 in the second transition zone 96. However, as above, the intermediate pitch P3 can alternatively decrease at a constant rate from P1 to P2 along the intermediate thread region 93.

It is to be appreciated that the equations discussed above can be used to calculate the number of revolutions N to, and the angular position A of, the predetermined transition location 95.

It is also to be appreciated that the methods described above can also be employed in similar fashion for forming, shaping, or otherwise preparing bone screw 102 with an automated thread-forming device In a second, non-limiting example embodiment, the bone screw 102 has a total length L1 of about 60 mm, a main head length L2 of about 2.7 mm, and a total head length L4 of about 5.0 mm. In this embodiment, the bone screw 102 defines the distal, proximal, and intermediate thread regions 91, 92, 93. The distal flank angle A1 is about 25°, the proximal flank angle A2 is about 5°, and the thread angle A3 is about 30°, and each of these angles A1, A2, A3 is substantially constant along each of the thread regions 91, 92, 93. The distal thread region 91 extends proximally from the distal end 8 of the bone screw 102 to a length L6 of about 12 mm and defines a constant distal pitch P1 of about 1.40 mm. The proximal thread region 92 extends distally from the proximal end 6 of the bone screw 102 to the predetermined transition location 95 at a length L7 of about 24.0 mm. The proximal thread region 92 defines a constant proximal pitch P2 of about 1.32 mm. The intermediate thread region 93 extends proximally from a shared boundary with the distal thread region 91 to a shared boundary with the proximal thread region 91 (i.e., the predetermined transition location 95) at a length L8 of about 24.0 mm. In this second example embodiment, the intermediate pitch P3 is substantially constant along length L8 and is about 1.36 mm. The main head portion 14a defines a minor thread diameter D3 of about 4.0 mm and a major thread diameter D4 of about 5.0 mm. The neck 14b tapers distally toward the central axis X at a neck taper angle A4 of about 22° to a minor thread diameter of about 2.5 mm. The tapered shaft portion 19 has a length L9 of about 19.0 mm and tapers distally from a minor thread diameter of about 2.5 mm to a minor thread diameter of about 2.3 mm, thus defining a taper angle A5 of about 0.30°. In this second example embodiment, the predetermined transition location 95 coincides with the distal end of the tapered shaft portion 19, although, in additional embodiments, the transition location 95 can be located anywhere along the tapered shaft portion 19. The main shaft portion 17 defines a minor thread diameter D1 of about 2.3 mm and a major thread diameter D2 (at least in the distal thread region 91) of about 4.0 mm. In this second example embodiment, the ratio of the distal pitch P1 to the proximal pitch P2 is about 1.061:1; the ratio of the main head length L2 to the total screw length L1 is about 0.045:1; the ratio of the total head length L4 to the total screw length L1 is about 0.083:1; the ratio of the main head minor thread diameter D3 to the main shaft minor thread diameter D1 is about 1.739:1; and the ratio of the main head major thread diameter D4 to the main shaft major thread diameter D2 is about 1.250:1.

The inventor has found, through her own testing, that the thread transition zone 94 and the predetermined transition location 95 as described above, in connection with the bone screw 2, 102 geometries described above (i.e., including a defined head 14), allows such bone screws 2, 102 to be manufactured on a multi-axis, multi-tool, high speed, CNC lathe. Additionally, employing a defined head 14 on the bone screw 2, 102, as opposed to a core having a limited increase in diameter to the proximal end of the screw, can allow for longer compression bone screws 2, 102 that require similar insertion torques to those currently available in the art. Moreover, the bone screws 2, 102 described herein, even at the upper end of the length ranges described above, can be employed without predrilling.

Another benefit is that the defined heads 14 described herein have been observed to provide a physician, during insertion, with enhanced tactile feedback when the head 14 achieves threaded engagement with bone material (and/or analogous material).

It is to be appreciated that the thread 20 of the head 14 of the bone screws 2, 102 described herein can be adapted for use with a bone plate. For example, the geometry of the head 14 and the thread 20 parameters along the head 14 can be adapted for locking with corresponding internal threads of a locking hole extending through a bone plate. In additional embodiments, the head 14 and the thread 20 thereof can be adapted for variable angle (VA) locking with respect to a bone plate.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone screw comprising a body extending from a proximal end to a distal end spaced from the proximal end in a distal direction, the body defining a central axis oriented along the distal direction, the body defining a core surface spaced from the central axis along a radial direction that is substantially perpendicular to the distal direction, the body further comprising:
   a head having a main head portion and a neck spaced from the main head portion in the distal direction, wherein the main head portion defines a main head length measured from the proximal end to an interface with the neck along the distal direction, and the core surface within the main head portion defines a minor head diameter value along the radial direction for substantially an entirety of the main head length;
   a shaft extending from the interface with the neck to the distal end in the distal direction, wherein the core surface at the shaft defines 1) a shaft length along the distal direction, and 2) a minor shaft diameter value along the radial direction for at least a majority of the shaft length, wherein the at least the majority of the shaft length extends in the distal direction from the interface with the neck, wherein the main head length is at least about 2.0 mm, the core surface along the neck defines a taper angle in a range of 18 degrees to 40 degrees, and a ratio of the minor head diameter value to the minor shaft diameter value is at least 1.5:1; and
   a thread extending outward from the core surface along the radial direction, the thread extending along a single, continuous, helical thread path that traverses at least a portion of the shaft, the neck, and at least a majority of the main head portion, the thread defining 1), a pitch region that extends along the shaft and defines a pitch of the thread, and 2) a second pitch region that extends from a shared boundary with the pitch region, encompasses the head, and defines a second pitch of the thread, wherein the second pitch is less than the pitch, and the pitch transitions to the second pitch at the shared boundary.

2. The bone screw of claim 1, wherein the bone screw defines a total screw length measured between the proximal and distal ends, and a ratio of the main head length to the total screw length is at least about 0.035:1 and about 0.15:1.

3. The bone screw of claim 1, wherein one or both of the minor head diameter value and the minor shaft diameter value is a respective substantially constant diameter.

4. The bone screw of claim 1, wherein the pitch region is an intermediate pitch region, the pitch is an intermediate pitch, and the thread further defines a first pitch region extending from the distal end to the intermediate pitch region, the first pitch region defining a first pitch of the thread, wherein the intermediate pitch is less than the first pitch.

5. The bone screw of claim 4, wherein a ratio of the first pitch to the second pitch is at least about 1.05:1.

6. The bone screw of claim 5, wherein the intermediate pitch is a variable pitch that decreases in a proximal direction that is opposite the distal direction.

7. The bone screw of claim 6, wherein the shared boundary is a second shared boundary at which the variable pitch is equivalent to the second pitch, and the intermediate pitch region and the first pitch region define a first shared boundary at which the variable pitch is equivalent to the first pitch.

8. The bone screw of claim 6, wherein;
   the first pitch region comprises a portion of the majority of the shaft length,
   the thread defines 1) a major head diameter value at the main head portion, and 2) a major shaft diameter value at the first pitch region, and
   a ratio of the major head diameter value to the major shaft diameter value is at least 1.2:1.

9. The bone screw of claim 4, wherein the thread defines a thread profile that is different in at least two of the pitch region, the second pitch region, and the intermediate pitch region.

10. The bone screw of claim 1, wherein the bone screw has a total length of at least about 50 mm along the distal direction.

11. The bone screw of claim 1, further comprising at least one of:
- a cannulation extending from the proximal end to the distal end along the central axis;
- a cutting flute extending to the distal end;
- a cutting flute that extends to the distal end and intersects the cannulation; and
- a cutting flute that extends to one or both of the proximal and distal ends.

12. The bone screw of claim 1, wherein the single, continuous, helical thread path extends in the distal direction from the proximal end of the body of the bone screw.

\* \* \* \* \*